United States Patent [19]

Schnabel

[11] Patent Number: 4,755,462

[45] Date of Patent: Jul. 5, 1988

[54] ANALYTICAL PROCESS AND AGENTS FOR THE DETECTION OF ESTEROLYTIC AND/OR PROTEOLYTIC ENZYMES

[75] Inventor: Eugen Schnabel, Wuppertal, Fed. Rep. of Germany

[73] Assignee: Miles Inc., Elkhart, Ind.

[21] Appl. No.: 710,625

[22] Filed: Mar. 11, 1985

[30] Foreign Application Priority Data

Apr. 6, 1984 [DE] Fed. Rep. of Germany ....... 3413120

[51] Int. Cl.$^4$ ............................ C12Q 1/44; C12Q 1/38
[52] U.S. Cl. ........................................ 435/19; 435/23; 435/805; 435/810
[58] Field of Search ...................... 435/19, 23, 24, 810, 435/20, 21, 805

[56] References Cited

U.S. PATENT DOCUMENTS

| | | | |
|---|---|---|---|
| 4,296,202 | 10/1981 | Berger et al. | 435/29 |
| 4,299,917 | 11/1981 | Berger et al. | 435/23 X |
| 4,331,760 | 5/1982 | Berger et al. | 435/19 |
| 4,469,789 | 9/1984 | Berger et al. | 435/23 |
| 4,551,428 | 11/1985 | Berger et al. | 435/23 X |

OTHER PUBLICATIONS

Magnusson, Bovine Prothrombin and Thrombin in Colowick et al., *Methods in Enzymology*, vol. XIX, Academic Press, N.Y., 1970, pp. 158–170.

*Primary Examiner*—Esther M. Kepplinger
*Assistant Examiner*—Shawn P. Foley
*Attorney, Agent, or Firm*—Roger N. Coe

[57] ABSTRACT

Agent for the detection of esterolytic and/or proteolytic enzymes, containing (a) an amino acid ester or peptide ester of a phenol, as the chromogenic enzyme substrate, and (b) a substance which accelerates the enzymatic cleavage of the amino acid ester or peptide ester bond of component (a), characterized in that it contains a polyamino acid with a molecular weight of between 1,000 and 2,000,000 as the accelerating substance.

10 Claims, No Drawings

ANALYTICAL PROCESS AND AGENTS FOR THE DETECTION OF ESTEROLYTIC AND/OR PROTEOLYTIC ENZYMES

The present invention relates to agents for analytical detection of esterolytic and/or proteolytic enzymes, for example in body fluids, the esters being incorporated into test agents, in particular test strips, in a suitable manner. Besides chromogenic enzyme substrates (aminoacid esters or peptide esters of suitable phenols) and, if appropriate, diazonium salts which couple with the phenols to form a colour, the agents according to the invention also contain polyaminoacids as accelerators for the enzymatic cleavage of the aminoacid esters or peptide esters. The agents are preferably used for the detection of leucocytes, in particular in urine.

The detection of leucocytes in body fluids, in particular in urine, is of great importance in the diagnostics of diseases of the kidneys and of the urogenital tract. This detection was originally carried out by counting the leucocytes in the noncentrifuged urine or in the urine sediment. In both methods, only intact leucocytes can be recorded. However, it is known that the rate of leucocytelysis is subject to wide variations, depending on the urine medium; thus, for example, in strongly alkaline urines the leucocyte half-life is only 60 minutes. This means that the leucocyte counts determined are too low. Apart from this lysis error, quantitative microscopic determination of the leucocytes in the noncentrifuged, homogenised urine gives very accurate values in the counting chamber. Nevertheless, this method is only rarely used in practice, since it is laborious and time-consuming and requires trained personnel.

The preferred process for leucocyte determinations in the urine in medical practice was therefore the so-called field of view method in the urine sediment. For this, the sample (sediment) first had to be obtained by centrifugation. However, other constituents of the urine were also thereby concentrated, and these—such as, for example, salts and epithelial cells—make microscopic counting of the leucocytes considerably more difficult. A varying sediment content, inhomogeneities of the sediment and a different optical design of the microscopes led to relatively large errors (up to several hundred percent) in stating the leucocyte count.

In order to avoid these difficulties, several attempts have already been made to use enzymatic reactions as the detection principle for leucocytes in various body fluids, since leucocytes have a widely spread enzyme spectrum.

Thus, for example, agents for the detection of leucocytes in body fluids are known from German Offenlegungsschriften (German Published Specification) Nos. 2,826,965 and 2,836,644, in which the esterolytic and/or proteolytic activity present in the leucocytes is utilised for analytical purposes. Sulphonphthaleine esters or azo dyestuff esters are used as substrates for the leucocyte esterases and/or proteases. The dyestuffs released in the enzymatic reaction are then determined by known methods. However, the agents described in these publications are still too insensitive for practical purposes, since their reaction times are too long with low leucocyte concentrations.

Various methods for the detection of proteases and esterases are also known from histochemical and phytochemical enzymology (compare, for example, A. G. E. Pearse, Histochemistry, Theoretical and Applied, 3rd edition, Churchill Livingstone, Edinburgh-London-New York 1968). In general, colourless or slightly coloured esters are used for the detection, these being split by the enzymes into a colourless acid and a similarly colourless alcohol (phenol) component. The phenol component is then converted into coloured products in a subsequent reaction, for example by coupling with diazonium salts or by oxidation. F. Schmalzl and H. Braunsteiner, for example, describe in Klin. Wschr. 46, 642 (1968) a specific phytochemical leucocyte esterase detection with naphthol-AS-D-chloroacetate as the substrate and a diazonium salt which forms a coloured azo compound with the naphthol liberated.

However, two-component systems of this type have proved to be unsuitable for rapid and simple detection of leucocytes in body fluids, such as, for example, in the urine, since they are much too insensitive: samples containing 5,000 leucocytes/$\mu$l still do not give a reaction.

British Pat. No. A-1,128,371 and European Pat. No. A-12,957 describe the use of indoxyl and thioindoxyl esters as chromogenic substrates for the detection of hydrolytic enzymes in body fluids. On enzymatic cleavage of the substrate, free indoxyl is formed, which is subsequently oxidised to the easily detectable blue dyestuff indigo. A commercially available test based on European Pat. No. A-12,957 consists of a strip of filter paper impregnated with N-tosyl-L-alanine-L-indoxyl ester. When the test strip is immersed in a urine sample containing leucocytes, it turns blue in colour. However, the long waiting time (about 15 minutes) before the end colouration is reached and the test can be evaluated is a considerable disadvantage of this product.

European Pat. No. A-14,929 describes various accelerators (pyridine derivatives; imidazole derivatives; alcohols; metal complexes) for the enzymatic cleavage reaction. However, the relatively long time before complete oxidation of the indoxyl and the low sensitivity of the test (detection limit: a few thousand leucocytes/$\mu$l) remain a disadvantage. The same applies to the use of esters of leuco-indoanilines as substrates for leucocyte enzymes according to European Pat. No. A-34,323.

European Pat. No. A-39,880 provides a combination of the substrates according to European Pat. Nos. A-12,957 and 14,929 with the detection principle of coupling with diazonium salts which has been discussed above. Although it is possible considerably to reduce the detection limits for leucocytes in this manner, the detection sensitivity of 15–20 leucocytes/$\mu$l which is desired for use in practice is still not achieved.

The object of the present invention was thus to discover new accelerators for ester-cleaving enzymes which, as a result of acceleration of the enzymatic cleavage of the substrates by the leucocyte enzymes, permit more sensitive and more rapid detection of the leucocytes in urine. This object is achieved by using polyaminoacids to the reagent system. Surprisingly, the polyaminoacids have a superior accelerating action on the leucocyte enzymes to that of the accelerators described in European Pat. No. A-14,929 (pyridine derivatives, imidazole derivatives, metal complexes and alcohols). In addition, they can also be used as detergents, so that simultaneous addition of detergents to the reagent systems used in practice (for example reaction solutions or formulations for the coating of test strips) is superfluous.

The invention relates to agents for the detection of esterolytic and/or proteolytic enzymes, containing (a) an aminoacid ester or peptide ester of a phenol, as the chromogenic enzyme substrate, (b) a substtance which accelerates the enzymatic cleavage of the aminoacid ester bond or peptide ester bond of component (a), if appropriate (c) a diazonium salt, if appropriate (d) a buffer, and if appropriate (e) a carrier and/or the usual additives, characterised in that component (b) is a polyaminoacid, preferably containing basic groups, with a molecular weight (number-average) of between 1,000 and 2,000,000.

Finally, the invention also relates to a process for the detection of esterolytic and/or proteolytic enzymes in liquid samples, in particular body fluids, which is characterised in that the sample is brought into contact with the agent according to the invention and the colour reaction which occurs is determined.

Both polyaminoacids which are built up from only a single aminoacid (homopolyaminoacids) and polycondensates of two or more different aminoacids in the form of copolyaminoacids with a randomised sequence of the constituent aminoacids or in the form of sequence polymers are suitable accelerators to be employed according to the invention. Sequence polymers are obtained in the polycondensation of peptides or their derivatives and have a defined, recurring aminoacid sequence. For the accelerating action of the polyaminoacids, it is particularly advantageous for at least one of the aminoacids used for the polymerisation or copolymerisation to carry a basic group, for example an amino group or guanido group.

Preferably, the polyaminoacids to be used according to the invention are built up from identical or different monomers of the general formula

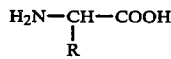  (I)

in which
R represents hydrogen or an optionally branched alkyl, cycloalkyl or aralkyl radical which has 1 to 15 C atoms, preferably 1 to 9 C atoms, and is optionally substituted by 1 or 2, in particular 1, hydroxyl, mercapto, carboxyl, amino or guanido groups.

The polyaminoacids to be used according to the invention as accelerators preferably contain 5 to 100 mole%, in particular 10 to 100 mole%, of monomer units with a basic group. Particularly preferred monomer units of this type are aminoacids of the general formula (I) which contain an amino or guanido group in the radical R. Examples of such basic aminoacids are, in particular, arginine, lysine and ornithine, which can be either in the racemic form or in the L- or D-form. The polyaminoacids and the sequence polymers can furthermore also contain as units basic aminoacids which do not occur in natural proteins. Examples which may be mentioned here are $\alpha,\gamma$-diaminobutyric acid, $\alpha,\beta$-diaminopropionic acid and the diaminopimelic acids.

The polyaminoacids to be used according to the invention as accelerators of the enzymatic cleavage are known from the literature and are commercially available, or they can be prepared by processes which are known per se (see, for example, E. Katchalski and M. Sela in: Advances of Protein Chemistry 13, 243–492 81958; and C. L. Anfinsen, M. L. Anson, J. T. Edsall and K. Bailey (Editors) in Academic Press Inc. Publishers, New York).

The average molecular weights (number-average) of the polyaminoacids should be between 1,000 and 2,000,000, and polyaminoacids with average molecular weights of 5,000 to 500,000 are preferably used, those with average molecular weights between 10,000 and 300,000 being particularly preferred.

The polyaminoacids are preferably employed in the homogeneous liquid test in concentrations of 0.0001% by weight to 1% by weight, and the concentrations are particularly preferably in the range from 0.001 to 0.01% by weight. In the preparation, described below, of test devices, they are used in concentrations of 0.05% by weight to 10% by weight, preferably 1 to 5% by weight, based on the impregnating solution. The polyaminoacids to be used according to the invention accelerate the enzymatic cleavage of the substrates described in European Pat. Nos. A-7,407, 8,428, 12,957, 14,929, 34,323 and 39,880 by the leucocyte enzymes, as well as the cleavage of the substrates which have already been described previously (G. Gomori, J. Histochem. Cytochem. 6 469 (1953); H. Löffler, Klin. Wochenschr. 39, 1120 (1961); L. Visser and E. Blout, Fed.-Proc. 28, 407 (1969) and Biochim. Biophys. Acta 268, 257 (1972), and F. Sweetman and L. Ornstein, J. Histochem. Cytochem. 23, 327 (1974)).

The preferred chromogenic substrates in the agents according to the invention also include the compounds described in a parallel Application, of the general formula (II)

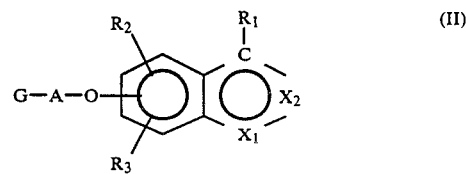

in which
$X_1$ and $X_2$ are identical or different and denote nitrogen and sulphur, with the proviso that $X_1$ and $X_2$ do not simultaneously represent sulphur;
$R_1$ represents hydrogen or an optionally branched alkyl group which has 1 to 6 carbon atoms and can optionally be substituted by halogen or hydroxyl;
$R_2$ and $R_3$ are identical or different and represent hydrogen, $C_1$–$C_6$-alkyl groups, $C_1$–$C_6$-alkoxy groups, $C_1$–$C_6$-acyl groups, halogen, trifluoromethyl, nitro, $SO_3H$, cyano, $C_1$–$C_8$-acylamino groups, $C_1$–$C_6$-dialkylamino groups or $C_6$–$C_{10}$-aryl groups, which can in turn be further substituted by $C_1$–$C_6$-alkyl groups, $C_1$–$C_6$-alkoxy groups, halogen, cyano, nitro, trifluoromethyl, $SO_3H$, $C_1$–$C_6$-acyl groups or $C_1$–$C_6$-dialkylamino groups, or
$R_2$ and $R_3$ together form a fused-on aromatic ring, preferably a benzene ring, which can in turn be substituted by 1 or 2 radicals $R_2$;
A denotes an aminoacid radical or peptide radical; and
G represents hydrogen or, preferably, a nitrogen-protective group which is usual in peptide chemistry or derived from such a group.

Preferred compounds of the general formula (II) are those in which $X_1$ represents sulphur and $X_2$ represents nitrogen. Compounds of the formula (II) in which $R_1$ represents hydrogen, and those in which $R_2$ and $R_3$, which are identical or different, represent hydrogen, $C_1$–$C_2$-alkyl, $C_1$–$C_2$-alkoxy, halogen, $C_1$–$C_4$-dialkylamino groups or benzene radicals are furthermore preferred.

The ester radical in the compounds of the formula (II) is particularly preferably in the 5-position.

Other chromogenic substrates which are preferred according to the invention are the compounds likewise described in a parallel Application, of the general formula (III)

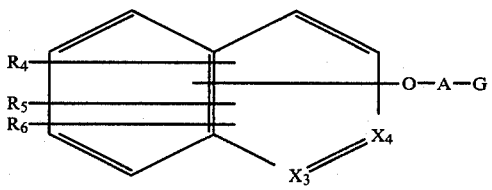

in which
  $X_3$ and $X_4$ represents N or CH, with the proviso that in each case either $X_3$ or $X_4$ represent N,
  $R_4$, $R_5$ and $R_6$ are identical or different and represent hydrogen, $C_1-C_6$-alkyl groups, $C_1-C_6$-alkoxy groups, $C_1-C_6$-acyl groups, halogen, trifluoromethyl, nitro, $SO_3H$, cyano, $C_1-C_8$-acylamino groups, $C_1-C_6$-dialkylamino groups or $C_6-C_{10}$-aryl groups, which can in turn be further substituted by $C_1-C_6$-alkyl groups, $C_1-C_6$-alkoxy groups, halogen, cyano, nitro, trifluoromethyl, $SO_3H$, $C_1-C_6$-acyl groups or $C_1-C_6$-dialkylamino groups, or
  $R_5$ and $R_6$ together form a fused-on aromatic ring, preferably a benzene ring, which can in turn be substituted by 1 or 2 radicals $R_4$, and
  A and G have the meaning given above in the case of the formula (II).

In the compounds according to the general formula (III), $X_3$ preferably represents CH and $X_4$ preferably represents nitrogen. $R_4$, $R_5$ and $R_6$, which can be identical or different, preferably represent hydrogen, $C_1-C_4$-alkyl, $C_1-C_4$-alkoxy, acylamino (where the acid radical can be aliphatic or aromatic with 1 to 6 C. atoms), $C_1-C_4$-dialkylamino, nitro, cyano, halogen, or aryl, which is optionally substituted by $C_1-C_4$-alkyl, $C_1-C_4$-alkoxy or halogen.

Particularly preferably, $R_4$, $R_5$ and $R_6$ are hydrogen, $C_1-C_4$-alkyl, phenyl or halogen, or $R_5$ and $R_6$ together form a fused-on benzene ring.

Suitable chromogenic substrates for the agents according to the invention are moreover also compounds of the general formula

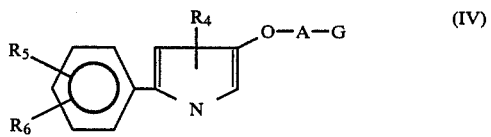

wherein
  $R_4$, $R_5$, $R_6$, A and G have the meaning given above in the case of formula (III).

In the general formulae (II), (III) and (IV), G-A—preferably represents a radical of the general formula

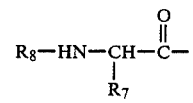

in which
  $R_7$ represents hydrogen or an optionally branched alkyl, cycloalkyl or aryl radical which has 1-15 C atoms, preferably 1-9 C atoms, and is optionally substituted by a hydroxyl, mercapto or carboxyl group, and
  $R_8$ represents hydrogen or, preferably, —CO-alkyl, —CO-aralkyl, —CO-aryl, —$SO_2$-alkyl or —$SO_2$-aryl, the alkyl radicals being straight-chain or branched with 1-9 C atoms, preferably 1-6 C atoms, and the aryl radicals preferably representing benzene rings, which are optionally substituted by $C_1-C_4$-alkyl groups, $C_1-C_4$-alkoxy groups or halogen.

G-A particularly preferably represents a radical, provided with a customary nitrogen-protective group, of a naturally occurring aminoacid or of a peptide of 2 to 8 such aminoacids.

The aminoacid radicals can be in their L- or D-form or in their racemic form here. Particularly preferred radicals are those of glycine, alanine, valine, leucine, isoleucine, phenylalanine, and tyrosine, the L-form being particularly preferred in each case. Any free hydroxyl group present can be acylated, preferably acetylated.

A peptide radical in the defintion of A is to be understood as meaning, for example, di-, tri-, tetra- and pentapeptides, preferably di- and tri-peptides, preferred possible aminoacid components being the abovementioned aminoacids.

The substrates of the general formulae (II), (III) and (IV) are obtained by reacting the corresponding phenols with aminoacids or peptides of the general formula

G-A-OH in which
  G and A have the abovementioned meaning, or suitable reactive derivatives thereof, by methods customary in peptide chemistry.

Examples of suitable reactive derivatives are the acid chlorides and the mixed anhydrides usually employed in peptide synthesis, for example with ethyl chloroformate or active esters, such as, for example, pentachlorophenyl esters or N-hydroxybenzotriazole esters.

The agents according to the invention preferably contain, as colour-forming agents which react with the phenols (liberated during enzymatic cleavage), diazonium salts of the general formula

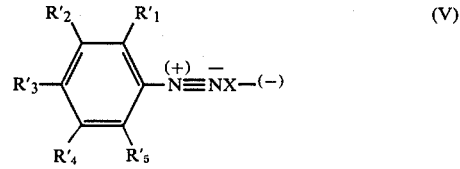

in which
  $R'_1$ denotes a lower alkyl, a lower alkoxy, a lower alkylmercapto, a hydroxy, nitro, cyano, trifluoromethyl, $C_1-C_8$-alkylsulphonamido, arylsulphonamido, $C_1-C_8$-alkylsulphone, arylsulphone, sulphonic acid or carboxylic acid, an N-morpholino, an N-thiomorpholino an N-pyrrolidino, an optionally N'-alkylated N-piperazino or N-piperidino group, halogen or hydrogen, $R'_3$ denotes a lower alkyl, a lower alkoxy, an aryloxy, a lower alkylmercapto, alkylamino or dialkylamino, a hydroxyl, nitro, cyano, $C_1$–$C_8$-alkylsulphonamido, arylsulphonamido, $C_1$–$C_8$-alkylsulphone, arylsulphone, sulphonic acid or carboxylic acid, an N-morpholino, N-thiomorpholino or N-pyrrolidino, an optionally N'-alkylated N-piperazino or N-piperidino or phenylamino group, a phenyl group which is optionaly substituted by a lower alkyl or lower alkoxy radical, halogen or hydrogen, $R'_2$, $R'_4$ and $R'_5$, which can be identical or different, each denote a lower alkyl, a lower alkoxy, nitro, $C_1$–$C_8$-alkylsulphonamido, arylsulphonamido, $C_1$–$C_8$-alkylsulphone, arylsulphone, sulphonic acid or carboxylic acid or a lower alkyl mercapto group, halogen or hydrogen, and X denotes a stabilising anion, it being possible for in each case 2 adjacent radicals $R'_1$ and $R'_5$ to be cyclised to form a benzene ring which is optionally substituted by halogen, a $C_1$–$C_6$-alkyl, a $C_1$–$C_6$-alkoxy or a nitro, sulphonic acid or carboxylic acid group, so that a diazonium salt of the naphthalene series is formed.

Preferably, in the general formula (V)

$R'_1$ represents $C_1$- to $C_4$-alkyl, $C_1$–$C_4$-alkoxy, hydroxyl, nitro, halogen or hydrogen;

$R'_3$ represents a $C_1$- to $C_4$-alkyl, $C_1$–$C_4$-alkoxy, aryloxy, $C_1$–$C_4$-alkylamino, $C_1$–$C_4$-dialkylamino, nitro, $C_1$–$C_4$-alkylsulphonamido, arylsulphonamido, $C_1$–$C_4$-alkylsulphone, arylsulphone, N-morpholino, N-pyrrolidino, phenylamino or sulphonic acid group or hydrogen; and $R'_2$, $R'_4$ and $R'_5$, which can be identical or different, represent $C_1$- to $C_4$-alkyl, $C_1$- to $C_4$-alkoxy, $C_1$- to $C_4$-alkylamino, $C_1$ to $C_4$-dialkylamino, nitro, $C_1$- to $C_4$-alkylsulphonamido, arylsulphonamido or sulphonic acid groups, halogen or hydrogen.

In each case 2 adjacent radicals $R'_1$ to $R'_5$ can here optionally be cyclised to give a benzene ring which is optionaly substituted by halogen or a $C_1$- to $C_4$-alkyl or $C_1$- to $C_4$-alkoxy or a nitro or sulphonic acid group.

In the context of the formula (V), aryl in each case represents an aromatic radical which has 6 to 12 C atoms, preferably 6 C atoms, and is optionally substituted by halogen or a $C_1$–$C_4$-alkyl or $C_1$–$C_4$-alkoxy group.

The diazonium salts of the general formula (V) are known per se, or they can be synthesised by methods which are known per se (Houben-Weyl, Methods of Organic Chemistry, volume X/3).

The agents, according to the invention, for the detection of proteolytic enzymes and, in particular, leucocyte enzymes preferably contain a suitable buffer system. Possible systems for this purpose are, for example, phosphate, borate, carbonate/bicarbonate, carbonate, barbiturate tris-(hydroxymethyl)-aminomethane (=tris), 2 amino-2-methyl-propane-1,3-diol (=amediol) or aminoacid buffer, the pH value and capacity as a rule being chosen such that a pH value of 6–10, preferably of 7–9, is established in the measurement solution or on the test strip.

In some cases, it may be advantageous also to conjointly use detergents in the agents according to the invention, in addition to the accelerating polyaminoacids.

These detergents on the one hand effect disintegration of the leucocytes present in the test solution and thus liberate the enzymes, and on the other hand act as solubilising agents for the substrates and the substances formed during cleavage, and, where relevant, intensify the colour. Possible detergents are both cationic and anionic detergents, as well as amphoteric and nonionic detergents.

Examples of these which may be mentioned are benzyl-dimethyl-tetradecyl-ammonium chloride, Na dodecylsulphate, zephirol, polyvinylpyrrolidone and heparinoid, and if appropriate mixtures of two or more of the abovementioned detergents can also be used. Since the polyaminoacids employed according to the invention as activators also have a detergent action, however, the addition of extra detergents can in principle be dispensed with.

It is particularly advantageous to use the above detergents in the determination of leucocytes by means of reagents fixed to a solid phase (for example a test strip), since a more homogeneous colour distribution and a more intensive colouration can thereby be achieved.

In the agents according to the invention, the reagents described above are preferably incorporated in an inert carrier of the type which is known per se, particularly preferred carrier matrices being porous materials, such as, in particular, filter paper, and also membranes made of plastic, glass-fibre mats (U.S. Pat. No. 3,846,247), porous ceramic strips, synthetic nonwoven fibres, spongy materials (U.S. Pat. No. 3,552,928), felt, textiles, wood, cellulose or silica gel.

For this purpose, the carriers mentioned are impregnated with a solution of the reagents described above in a suitable solvent which can easily be removed, for example water, methanol, ethanol, acetone, dimethylformamide or dimethylsulphoxide. This is preferably effected in two separate steps: the material is first impregnated with an aqueous solution containing the buffer and other water-soluble additives. It is then impregnated with a solution of the chromogenic enzyme substrates of the general formula (V) and activators. However, the impregnation can also be carried out in another sequence, or with a different composition of the two impregnating solutions. Preferably, the impregnating solution or the fluid to be investigated contains the chromogenic substrate and the diazonium salt in each case in a concentration of $10^{-4}$ to $10^{-1}$ mole/liter, in particular $10^{-3}$ to $10^{-2}$ mole/liter, and the polyaminoacid in a concentration of 0.05% by weight to 10% by weight, in particular 1% by weight to 5% by weight.

When filter paper is used as the matrix, the finished test papers can be used as such or they can be stuck onto handles in a manner which is known per se or, preferably, sealed between plastics and fine-mesh networks, for example according to DE-OS (German Published Specification) No. 2,118,455.

To produce test strips coated with film, preferably all the reagents are introduced into the solution or dispersion of a film-forming substance, such as, for example, a polyvinyl ester or polyamide, and are homogeneously mixed. A thin layer of the mixture is brushed onto a carrier made of plastic and dried. After drying, the film-coated test strips thus produced are cut and can be used as such or stuck onto handles in a manner which is known per se, or, for example, sealed between plastics and fine-mesh networks according to DE-OS (German Published Specification) No. 2,118,455.

A diagnostic agent according to the invention for the detection of esterolytic and/or proteolytic enzymes, in particular leucocyte enzymes, can be prepared in the form of powder mixtures or reagent tablets by adding the usual pharmaceutical additives to the abovementioned constituents of the test agent and granulating the mixture. Examples of additives of this type are carbohydrates, such as, for example, mono-, oligo- or poly-saccharides, or sugar-alcohols, such as, for example, mannitol, sorbitol or xylitol, or other soluble inert compounds, such as polyethylene glycols or polyvinylpyrrolidone. The powder mixtures or reagent tablets have, for example, a final weight of about 50–200 mg, preferably 50–80 mg.

To prepare lyophilisates with a total weight of in each case about 5–20 mg, preferably about 10 mg, a solution which, in addition to all the reagents required for the test, contains the usual structure-forming agents, such as, for example, polyvinylpyrrolidone, and if appropriate other fillers, such as, for example, mannitol, sorbitol or xylitol, is freeze-dried.

A diagnostic agent according to the invention in the form of a solution preferably contains all the reagents required for the test. Possible solvents are water and mixtures of water with a water-soluble organic solvent, such as, for example, methanol, ethanol, acetone or dimethylformamide. For storage reasons, it may be advantageous to divide the reagents required for the test into two or more solutions, which are only brought together during the actual investigation.

The diagnostic agents thus prepared permit, after immersion in the body fluid to be investigated or after addition to the body fluid in question, rapid and simple detection of the presence of esterolytic and/or proteolytic enzymes, in particular leucocyte enzymes, via colour formation, which can be measured visually or photometrically, for example by reflectance photometry or in a cell. Since the activity of the leucocyte enzymes per cell can be regarded as an essentially constant parameter, the leucocyte concentration of the body fluid investigated can be determined from the intensity of the colour formation. Both intact and lysed leucocytes are thereby recorded with the diagnostic agent according to the invention, since the activity of the leucocyte enzymes is fully retained even after lysis of the leucocytes. Consequently, no lysis error occurs.

The following examples serve to illustrate the present invention. Unless indicated otherwise, the amounts given are to be understood as parts by weight or percentages by weight.

GENERAL PROCEDURE

Depending on the substrate, 50–250 μl of N-methylpyrrolidone were added, as the solubilising agent, to 2.25 ml of the buffer in question and the volume of the solution was made up to 2.5 ml with buffer. 5 μl of a solution of 5–100 mg of polyaminoacid in 1 ml of water or N-methylpyrrolidone and 5 μl of a solution of 2 mg of Na dodecylsulphonate (SDS) or 4 mg of the other detergents in 1 ml of water or N-methylpyrrolidone were then added. After good thorough mixing, 5 μl of a $10^{-1}$ molar substrate or solution in N-methylpyrrolidone or the stated solvent were added and, after addition of the leucocyte suspension, the increase in extinction at the stated wavelength was monitored continuously. In a parallel batch without the addition of leucocytes, the increase in extinction caused by spontaneous hydrolysis is determined.

To determine the rate of reaction, the increase in extinction obtained in the enzyme reaction is reduced by the value found for spontaneous hydrolysis. Absolute values for cleavage of the substrate (moles/minute) can be calculated from the extinction differences with the aid of the molar extinction coefficients.

EXAMPLE 1

Influence of the addition of polyaminoacids on the rate of cleavage of tosyl-L-alanine indoxyl ester by leucocytes in 0.1M tris-(hydroxymethyl)-aminomethane buffer, pH 8.8 (addition of 50 μl of N-methylpyrrolidone per test batch). The cleavage rates were determined by continuous measurement of the increase in extinction at 360 nm.

TABLE 1

| Activator | μg/Test | relative rate of cleavage |
|---|---|---|
| Decanol | 125 | 1 |
| Poly-L-Arg (40,000) | " | 1.75 |
| Poly-D-Lys (100,000) | " | 2.05 |
| Poly-DL-Lys (37,000) | " | 3.10 |
| Poly-L-Lys (14,000) | " | 1.82 |
| Poly-L-Lys (22,000) | " | 1.94 |
| Poly-L-Lys (55,000) | " | 2.37 |
| Poly-L-Lys (100,000) | 50 | 2.10 |
| Poly-L-Lys (100,000) | 125 | 2.35 |
| Poly-L-Lys (100,000) | 250 | 2.50 |
| Poly-L-Lys (260,000) | 125 | 1.82 |
| Poly-L-Lys (520,000) | 50 | 1.75 |
| Poly-L-Lys (520,000) | 125 | 2.20 |
| Poly-L-Lys (520,000) | 250 | 2.10 |
| Poly-(L-Lys, L-Ala) = 2:1 (32,000) | 50 | 1.75 |
| Poly-(L-Lys, L-Ala) = 2:1 (32,000) | 125 | 1.90 |
| Poly-(L-Lys, L-Ala) = 2:1 (32,000) | 250 | 2.00 |
| Poly-L-Orn (30,000) | 125 | 1.80:2.90 |

The average molecular weights (number-average) of the polyaminoacids are given in parentheses.

10 μg of SDS per test batch were also used in each case as the detergent.

EXAMPLE 2

Acceleration of the cleavage of 5-[N-tosyl-L-alanyloxy]-1,2-benzisothiazole by leucocytes on addition of polyaminoacids in 0.1M tris-(hydroxymethyl)-aminomethane buffer, pH 8.4, in the presence of 100 μl of N-methylpyrrolidone per test batch. The rates of cleavage were determined by continuous measurement of the increase in extrinction at 355 nm.

TABLE 2

| Activator | μg/Test | relative rate of cleavage |
|---|---|---|
| Decanol | 125 | 1.0 |
| Poly-L-Arg (40,000) | 25 | 2.4 |
| Poly-L-Arg (40,000) | 30 | 3.6 |
| Poly-L-Arg (40,000) | 125 | 3.7 |
| Poly-L-Arg (40,000) | 250 | 3.4 |
| Poly-L-Lys (14,000) | 125 | 7.8 |
| Poly-L-Orn (30,000) | 125 | 7.0 |
| Poly-L-Arg (40,000) | 25 | 3.0 |
| Poly-L-Arg (40,000) | 50 | 2.8 |
| Poly-L-Arg (40,000) | 125 | 4.0 |
| Poly-L-Arg (40,000) | 250 | 3.3 |
| Poly-L-Arg (40,000) | 375 | 3.4 |
| Poly-L-Arg (40,000) | 500 | 3.2 |
| Poly-L-Lys (14,000) | 500 | 5.6 |
| Poly-L-Orn (30,000) | 500 | 4.3 |

TABLE 2-continued

| Activator | μg/Test | relative rate of cleavage |
|---|---|---|
| Poly-L-Arg (40,000) | 500 | 2.95; 2.4 |
| Poly-L-Lys (14,000) | 500 | 3.4 |
| Poly-L-Orn (30,000) | 500 | 3.0 |

The average molecular weights (number-average) of the polymers are given in parentheses.

SDS or, in the last three experiments of Table 2, zephirol (as an approximately 50% strength aqueous solution) were added as the detergent, in each case in an amount of 10 μg per test batch.

EXAMPLE 3

Acceleration of the cleavage of tosyl-L-alanine 3-hydroxy-5-phenylpyrrole ester by leucocytes on addition of polyaminoacids of 0.1M tris-(hydroxymethyl)-aminomethane, buffer, pH 8.8, in the presence of 250 μl of N-methylpyrrolidone per test batch. The rates of cleavage were determined by continuous measurement of the increase in extinction at 330 nm.

TABLE 3

| Activator | μg/Test | relative rate of cleavage |
|---|---|---|
| Decanol | 125 | 1.0 |
| Poly-L-Arg (40,000) | 20 | 3.6 |
| Poly-L-Arg (40,000) | 125 | 4.4 |
| Poly-DL-Lys (37,000) | 125 | 4.3 |
| Poly-D-Lys (100,000) | 125 | 4.5 |
| Poly-L-Lys (14,000) | 20 | 3.7 |
| Poly-L-Lys (14,000) | 125 | 4.8; 6.9 |
| Poly-L-Lys (260,000) | 125 | 4.55 |
| Poly-(L-Lys$_2$,L-Ala) (32,000) | 125 | 4.65 |
| Poly-L-Orn (30,000) | 20 | 3.7 |
| Poly-L-Orn (30,000) | 125 | 5.75; 6.9 |

The average molecular weights (number-average) of the polyaminoacids are given in parentheses.

10 μg of SDS per test batch was added in each case as the detergent.

EXAMPLE 4

Acceleration of the enzymatic cleavage of tosyl-L-alanine 3-hydroxy-5-phenolpyrrole ester by leucocytes on addition of polyaminoacids in 0.1M tris-(hydroxymethyl)-aminomethane buffer, pH 8.4, in the presence of 250 μl of N-methylpyrrolidone per test batch. The rates of cleavage were determined by continuous measurement of the increase in extinction at 325 nm.

TABLE 4

| Activator | μg/Test | Detergent | μg/Test | relative rate of cleavage |
|---|---|---|---|---|
| Decanol | 125 | SDS | 10 | 1 |
| Poly-L-Arg (40,000) | 125 | — | — | 4.8 |
| Poly-DL-Lys (37,000) | 125 | — | — | 4.8 |
| Poly-L-Lys (14,000) | 125 | — | — | 3.7 |
| Poly-L-Arg (40,000) | 50 | SDS | 10 | 6.0 |
| Poly-L-Arg (40,000) | 125 | SDS | 10 | 6.65 |
| Poly-L-Arg (40,000) | 125 | BDTA | 20 | 4.05 |
| Poly-L-Arg (40,000) | 125 | heparinoid | 20 | 5.15 |
| Poly-DL-Lys (37,000) | 125 | heparinoid | 20 | 6.55 |
| Poly-L-Arg (40,000) | 50 | zephirol | 20 | 6.35 |

SDS = sodium dodecyl-sulphate
BDTA = benzyl-dimethyl-tetradecyl-ammonium chloride Zephirol was used as an approximately 50% strength solution.

The average molecular weights (number-average) of the polymers are given in parentheses.

General operating instructions for the preparation of the N-tosyl-L-alanyl esters The esters were in each case prepared by reacting N-tosyl-L-alanyl chloride with the phenols in absolute methyl ethyl ketone or absolute toluene in the presence of powdered potassium carbonate. After stirring at about 55° C. for 6 to 12 hours, between 40 and 70% of the phenol had reacted. The molar ratio of phenol:K$_2$CO$_3$:acid chloride was usually 1:1.5:1.5. The pH value was about 7 throughout the entire reaction time. For working up, the potassium carbonate was filtered off at 50° C. and the solvent was then distilled off in vacuo. The product was purified via column chromatography with silica gel-eluant (petroleum ether:acetone=about 9:1) and subsequent recrystallisation.

p-Tosyl-L-alanine

Literature: E. Fischer and W. Lipschitz, B. 48, 362 (1915).

83.7 g (0.93 mole) of L-alanine are dissolved in 465 ml of approximately 2N sodium hydroxide solution. 186 g (0.976 mole) of p-toluenesulphonyl chloride are added to the solution in portions at 70°-72° C. in the course of 20 minutes. During the addition of the sulphonyl chloride, the reaction mixture is kept at pH 10 with approximately 2N sodium hydroxide solution by means of an automatic titrator; 560 ml of 2N sodium hydroxide solution are consumed here. When the pH of the reaction mixture no longer changes, the mixture is cooled to 15°-5° C. and brought to pH 3 with 37% strength hydrochloric acid. The product which has separated out is filtered off with suction and the moist filter cake is recrystallised from 2,350 ml of water.

Yield: 185.5 g (82% of theory) of L-p-tosylalanine of melting point 132°-135° C.

p-Tosyl-L-alanyl chloride 158.1 g (0.65 mole) of p-tosyl-L-alanine are stirred in 350 ml of thionyl chloride at 40° C., until a clear solution has formed. The excess thionyl chloride is then distilled off under a waterpump vacuum. The residue in the flask is taken up in 300 ml of distilled toluene. A clear, slightly yellowish solution is obtained, which is poured into 900 ml of stirred ligroin. The acid chloride precipitates. The following day, it is filtered off with suction, washed with light gasolene and dried in a vacuum desiccator over calcium chloride/potassium hydroxide.

Yield: 155 g (91% of theory) of almost colourless crystals of melting point 81°-83° C.

What is claimed is:

1. Agent for the detection of esterolytic or proteolytic enzymes, consisting essentially of (a) an amino acid ester or peptide ester of a phenol, as the chromogenic enzyme substrate, and (b) a substance which acclerates the enzymatic cleavage of the amino acid ester or peptide ester bond of component (a), wherein said substance is an accelerating amount of a polyamino acid with a molecular weight of between 1,000 and 2,000,000.

2. Agent according to claim 1, in which the molecular weight of the polyamino acid is between 5,000 and 500,000.

3. Agent according to claim 1 or 2, in which the polyamino acid is built up from only one amino acid.

4. Agent according to claim 1 or 2, in which the polyamino acid is built up from at least two different amino acids in random sequence.

5. Agent according to claim 1 or 2, in which the polyamino acid is built up from at least two different amino acids with a recurring amino acid sequence.

6. Agent according to claim 1 in which the polyamino acid is built up from amino acids of the general formula

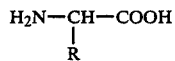

in which R represents hydrogen or a branched alkyl, cycloalkyl or aralkyl radical which has 1 to 15 carbon atoms, which can be substituted by 1 to 2 hydroxyl, mercapto, carboxyl, amino or guanido groups.

7. Agent according to claim 6, in which 5 to 100 mole%, of the amino acid units of the polyamino acid carry a basic group.

8. Agent according to claim 7, in which the basic groups are amino or guanido groups.

9. Agent according to claim 1, which is the reagents are incorporated in an inert carrier.

10. Process for the detection of esterolytic or proteolytic enzymes in a liquid sample wherein the sample is brought into contact with an agent according to claim 1 and the color reaction which occurs is determined.

* * * * *